United States Patent
Hathaway et al.

(10) Patent No.: US 10,314,487 B2
(45) Date of Patent: Jun. 11, 2019

(54) DIFFRACTION GRATING FOR WAVELENGTH SELECTION IN LINE-SCAN SLO

(71) Applicant: Cellview Imaging, Inc., Toronto (CA)

(72) Inventors: Mark Hathaway, Canterbury (GB); Rishard Weitz, Toronto (CA)

(73) Assignee: Cellview Imaging Inc. (CA)

( * ) Notice: Subject to any disclaimer, the term of this patent is extended or adjusted under 35 U.S.C. 154(b) by 0 days.

(21) Appl. No.: 15/318,203

(22) PCT Filed: Jun. 11, 2015

(86) PCT No.: PCT/CA2015/000372
§ 371 (c)(1),
(2) Date: Dec. 12, 2016

(87) PCT Pub. No.: WO2015/188256
PCT Pub. Date: Dec. 17, 2015

(65) Prior Publication Data
US 2017/0127940 A1    May 11, 2017

Related U.S. Application Data

(60) Provisional application No. 62/010,656, filed on Jun. 11, 2014.

(51) Int. Cl.
*G02B 26/00* (2006.01)
*A61B 3/12* (2006.01)
(Continued)

(52) U.S. Cl.
CPC .......... *A61B 3/1225* (2013.01); *A61B 3/0008* (2013.01); *A61B 3/1025* (2013.01);
(Continued)

(58) Field of Classification Search
CPC .......... A61B 3/135; A61B 3/12; A61B 3/117; A61B 3/1225; A61B 3/1025;
(Continued)

(56) References Cited

U.S. PATENT DOCUMENTS 5,216,680 A * 6/1993 Magnusson .......... G02B 5/1828
372/102
6,583,873 B1   6/2003 Goncharov et al.
(Continued)

OTHER PUBLICATIONS

Gramatikov, Boris I., Modern Technologies for Retinal Scanning and Imaging: An Introduction for the Biomedical Engineer, Biomedical Engineering Online, Biomed Central Ltd, vol. 13, No. 1, Apr. 2014, p. 52, XP021186482.

*Primary Examiner* — William R Alexander
*Assistant Examiner* — Henry A Duong
(74) *Attorney, Agent, or Firm* — Laubscher & Laubscher, P.C.

(57) ABSTRACT

In line-scan scanning laser ophthalmoscopy (SLO) a narrowband of wavelengths is required. For greater flexibility the frequencies of this narrowband should be selectable. This is possible using a broadband tunable single mode source, but such a solution is expensive. A system is provided in which an extended broadband source is used. Light from the extended source passes to a diffraction grating, which introduces a wavelength dependent angular separation when reflecting the light. By rotating the diffraction grating, only light of a selectable narrowband passes through a fixed output slit for use by the line-scan SLO system. Alternatively, the diffraction grating can be fixed and a rotatable mirror lying between the diffraction grating and the output slit can be used to select the wavelengths reaching the line-scan SLO system.

8 Claims, 2 Drawing Sheets

(51) Int. Cl.
*A61B 3/00*       (2006.01)
*A61B 3/10*       (2006.01)
*G02B 26/10*      (2006.01)
*G02B 26/08*      (2006.01)
*G02B 27/42*      (2006.01)

(52) U.S. Cl.
CPC ..... *G02B 26/0808* (2013.01); *G02B 26/0816* (2013.01); *G02B 26/106* (2013.01); *G02B 27/4227* (2013.01)

(58) Field of Classification Search
CPC ..... A61B 3/0008; A61B 3/1208; A61F 9/008; G02B 27/4227; G02B 26/0816; G02B 26/0808; G02B 26/106
USPC ......................................................... 351/214
See application file for complete search history.

(56) References Cited

U.S. PATENT DOCUMENTS

| | | | | |
|---|---|---|---|---|
| 8,063,409 B2* | 11/2011 | Peng | ................ | G02B 27/1006 257/431 |
| 2013/0176535 A1 | 7/2013 | Mensink et al. | | |
| 2014/0160488 A1* | 6/2014 | Zhou | ................ | G01B 9/02004 356/479 |

\* cited by examiner

DIFFRACTION GRATING FOR WAVELENGTH SELECTION IN LINE-SCAN SLO

FIELD OF INVENTION

This invention relates to selection of wavelengths from an extended source, in particular selection of a narrowband of wavelengths for use in line-scan scanning laser ophthalmoscopy.

BACKGROUND

In line-scan scanning laser ophthalmoscopy (SLO) systems a line of light is used to illuminate a patient's retina at a variety of places, rather than a small spot as is used in a confocal SLO system. If the frequency of this line of light is to be adjustable, one solution would be to use separate lasers as the source of light and to select among the lasers. In fact this is what is done in some confocal SLO systems. However this provides only discrete frequencies of light, and the use of multiple lasers increases both the size and cost of the SLO system. Another solution would be to use a tunable laser. However while this would provide a more continuous selection of frequencies, the use of a tunable laser increases the cost of the SLO system even more.

There is a need to provide a line-scan SLO system which allows selection of a narrowband of wavelengths from a large range of wavelengths, without requiring the high cost of tunable lasers.

SUMMARY

By using a diffraction grating and the disclosed arrangement of lenses and slits, an extended source emitting light over a broadband of wavelengths can be used as a light source for a line-scan SLO system while allowing the wavelength of light illuminating the patient's retina to be tunable. Use of an extended source as the source of light is less expensive than using point sources. Rotation of the diffraction grating presents different wavelengths to an output slit, thereby allowing the wavelengths passing through the output slit to be selectable. Alternatively, the diffraction grating can be fixed and a mirror rotated in order that only some of the wavelengths reach the output slit.

BRIEF DESCRIPTION OF THE DRAWINGS

The features and advantages of embodiments of the invention will become more apparent from the following detailed description of the preferred embodiment(s) with reference to the attached figures, wherein.

It is noted that in the attached figures, like features bear similar labels.

DETAILED DESCRIPTION OF THE PREFERRED EMBODIMENTS

Figure 1:
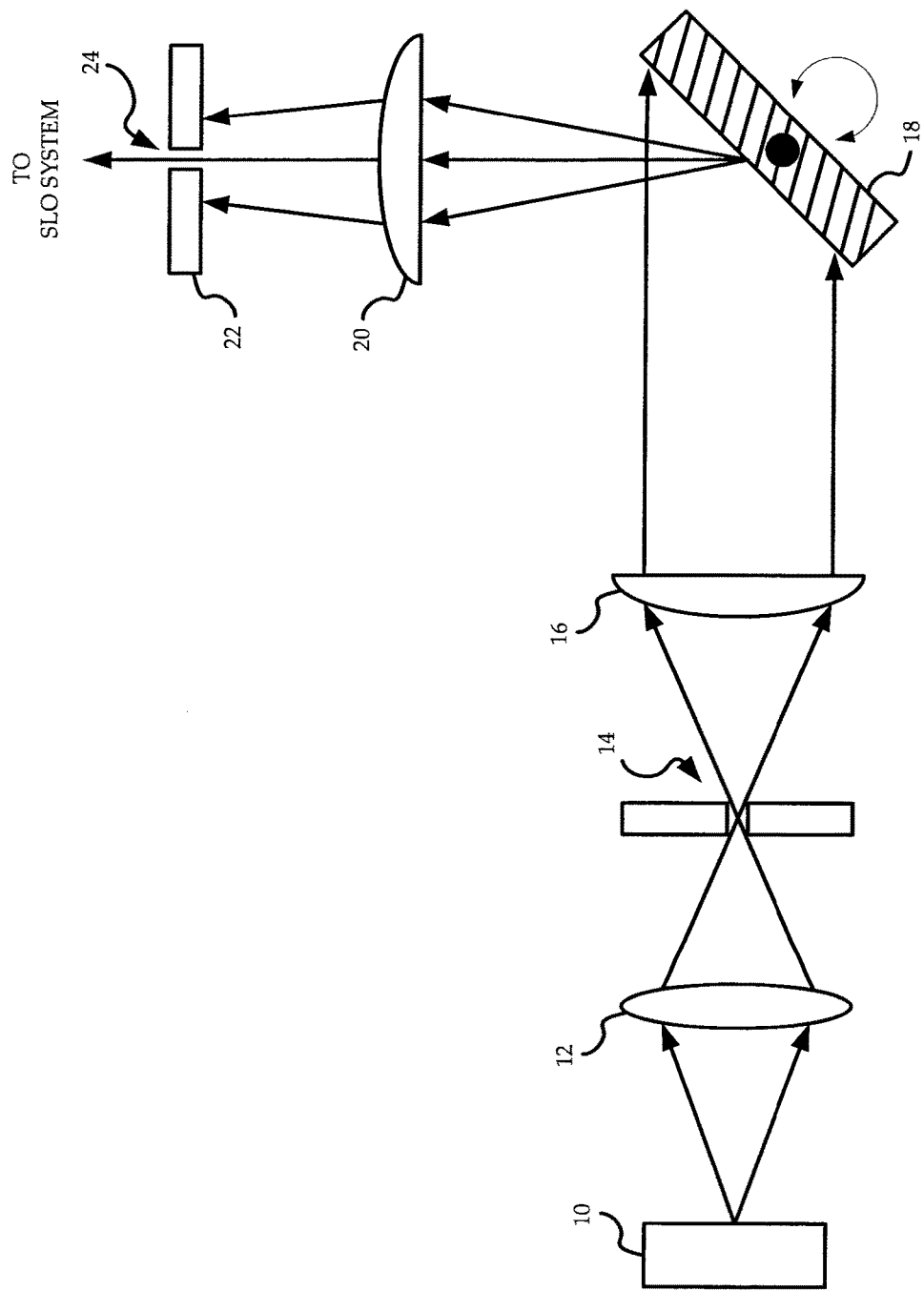
FIG. 1 shows a system for presenting selected wavelengths to an output slit according to one embodiment of the invention.

Referring to FIG. 1, a system for presenting selected wavelengths to an output slit according to one embodiment of the invention is shown. An extended broadband source 10 generates light over a broad range of wavelengths. Extended sources are typically less expensive than single mode sources, especially tunable single mode sources. The extended source 10 may be a plurality of light emitting diodes (LEDs), the number and type of LEDs used depending on the spectral range desired. The plurality of LEDs causes the source 10 to be extended but generates light covering a large spectral range. Alternatively, the source 10 may be a single broadband extended source of light. In either case, the breadth of the bandwidth of light produced by the source 10 dictates the tuning range of the system.

Light from the extended source 10 enters a first lens 12, which converges the light to an input slit 14. The light passes through the input slit 14 and reaches a second lens 16. The second lens 16 directs the light at a diffraction grating 18. In this way, the diffraction grating 18 receives all, or a large portion, of the light emitted in the direction of the diffraction grating 18.

The light reaching the diffraction grating 18 is both spread laterally and covers a large spectral range. The diffraction grating 18 introduces a wavelength-dependent angular separation to the light, i.e. the angle at which different wavelengths of light reflect off the diffraction grating 18 differs. The wavelength-separated light reaches a third lens 20. The third lens 20 focuses the light on a screen 22 containing an output slit 24. Because different wavelengths of the light reach the third lens 20 at different angles, each wavelength of light comes to a focus at a different position of the screen 22. Only wavelengths of light hitting the third lens 20 near its center are focused onto the output slit 24. In this way only a narrow band of light passes through the output slit 24 to a further system, such as a line-scan scanning laser ophthalmoscopy (SLO) system, even though a broadband source 10 was used.

The diffraction grating 18 is rotatable relative to the extended source 10 and the output slit 24. By rotating the diffraction grating 18, different wavelengths of light reach the center of the third lens 20 and are focused on the output slit 24, so as to pass through the output slit 24. If it is desired to use a particular wavelength (or more accurately, a particular narrow band of wavelengths) at the further system, then the diffraction grating 18 can be rotated to the position which causes light of the desired wavelength to focus onto the output slit 24. A person of ordinary skill in the art would know at what angle to position the diffraction grating 18 and what grating spacing to use, using the grating equation and the incident wavelengths of light.

Figure 2:
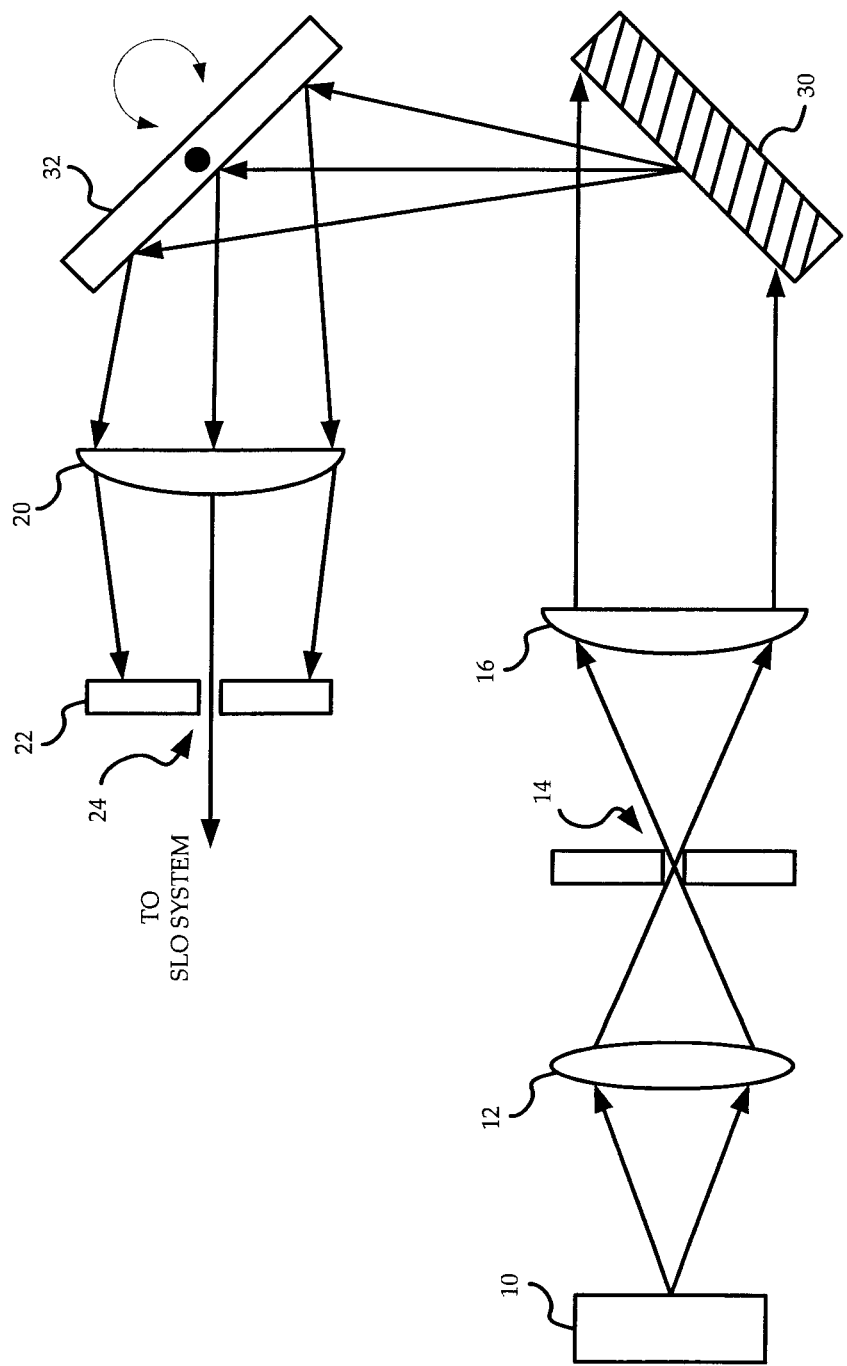
FIG. 2 shows a system for presenting selected wavelengths to an output slit according to another embodiment of the invention.

In the embodiment described above, the rotational position of the diffraction grating 18 relative to the output slit 24 determines which narrow band of light within the broadband of light emitted by the extended source 10 reaches the output slit 24. Alternatively, the rotational position of a different component within the system can be used to determine the particular narrow band of light reaching the output slit 24. Referring to FIG. 2, a system for presenting selected wavelengths to an output slit according to another embodiment of the invention is shown. The system is similar to that described above with reference to FIG. 1. A wavelength-dependent angular separation of light from a broadband extended source 10 is still provided by a diffraction grating 30. However in the embodiment described with reference to FIG. 2 the diffraction grating 30 is in a fixed position. The desired wavelength is directed to the output slit 24 by a rotatable mirror 32. The rotational position of the mirror 32 relative to the output slit 24 determines the particular narrow band of light reaching the output slit 24, allowing selection of the wavelengths of light reaching the output slit 24 by rotation of the mirror 32. The mirror is substantially planar.

By rotating the rotatable component, either the diffraction grating or the mirror, depending on the embodiment, to a rest position, the frequencies passed to and received by the output slit can be selected as a narrow band of light even though the source 10 produces a broadband of light.

The systems described above may be used to implement a method of producing a narrow band of light for use in a line-scan SLO system. A broadband of light is emitted from an extended source. An angular separation of the frequencies of the broadband is produced using a diffraction grating. A component is rotated so as to direct a selected narrow band of light containing a subset of the frequencies within the broadband towards an output slit. The component being rotated may be the diffraction grating, or may be a mirror placed so as to direct some light from the diffraction grating towards the output slit.

The embodiments presented are exemplary only and persons skilled in the art would appreciate that variations to the embodiments described above may be made without departing from the spirit of the invention. The scope of the invention is solely defined by the appended claims.

We claim:

1. A system comprising:
   a broadband extended source;
   a diffraction grating positioned to receive a broadband of light from the extended source;
   a rotatable mirror; and
   an output slit able to receive one of different narrow bands of light reflected by the diffraction grating, each narrow band of light determined by a different rotational position of the rotatable mirror relative to the output slit, wherein the diffraction grating is in a fixed position.

2. The system of claim 1 wherein the rotatable mirror is positioned so as to be able to reflect light reflected by the diffraction grating towards the output slit.

3. The system of claim 1 wherein the rotatable mirror is a substantially planar mirror.

4. The system of claim 1 wherein the output slit passes the narrow band of light to a line-scan scanning laser ophthalmoscopy (SLO) system.

5. The system of claim 1 wherein the rotatable mirror is at rest during reception of the narrow band of light by the output slit.

6. A method of producing a narrow band of light for use in a line-scan scanning laser ophthalmoscopy (SLO) system, the method comprising:
   emitting a broadband of light from an extended source;
   producing an angular separation of the frequencies of the broadband f light using a diffraction grating; and
   rotating a mirror so as to direct a selected narrow band of light containing a subset of the frequencies within the broadband of light towards an output slit, wherein the diffraction grating is in a fixed position.

7. The method of claim 6 wherein the mirror is a substantially planar mirror.

8. The method of claim 6 wherein rotating the mirror comprises rotating the mirror to a rest position.

\* \* \* \* \*